(12) United States Patent
Muir et al.

(10) Patent No.: US 6,197,075 B1
(45) Date of Patent: Mar. 6, 2001

(54) OVERBASED MAGNESIUM DEPOSIT CONTROL ADDITIVE FOR RESIDUAL FUEL OILS

(75) Inventors: Ronald J. Muir, West Hill; Theo I. Eliades, Scarborough, both of (CA)

(73) Assignee: Crompton Corporation, Greenwich, CT (US)

( * ) Notice: Subject to any disclaimer, the term of this patent is extended or adjusted under 35 U.S.C. 154(b) by 0 days.

(21) Appl. No.: 09/054,005

(22) Filed: Apr. 2, 1998

(51) Int. Cl.$^7$ ............................ C10L 1/18; C10M 129/00
(52) U.S. Cl. .................... 44/373; 44/331; 44/450; 508/391; 508/398; 508/460
(58) Field of Search .................... 508/232, 391, 508/398, 460, 506, 312; 44/331, 373, 450

(56) References Cited

U.S. PATENT DOCUMENTS

| | | | |
|---|---|---|---|
| 3,629,109 | * 12/1971 | Gergel | 508/402 |
| 3,994,699 | 11/1976 | Scott | 44/76 |
| 4,056,479 | 11/1977 | Redmore et al. | 252/18 |
| 4,129,589 | * 12/1978 | Eliades et al. | 508/333 |
| 4,131,433 | 12/1978 | Scott | 44/57 |
| 4,502,970 | * 3/1985 | Schetelich et al. | 508/192 |
| 4,617,135 | 10/1986 | Muir | 252/33.2 |
| 4,647,387 | * 3/1987 | Muir | 508/391 |
| 4,931,164 | 4/1990 | Dickakian | 208/48 AA |
| 5,561,977 | 10/1996 | Harada et al. | 60/39.02 |
| 5,658,862 | 8/1997 | Vrahopoulou | 508/192 |

FOREIGN PATENT DOCUMENTS

| | | |
|---|---|---|
| 2014880 | 10/1970 | (DE) . |
| 0347103 | 12/1989 | (EP) . |
| 0586254 | 3/1994 | (EP) . |
| 0604232 | 6/1994 | (EP) . |
| 2303063 | 10/1976 | (FR) . |
| 2580291 | 10/1986 | (FR) . |
| WO 8909812 | 10/1989 | (WO) . |
| WO 9638518 | 12/1996 | (WO) . |

OTHER PUBLICATIONS

PCT Search Report for corresponding PCT application dated Jul. 5, 1999.

* cited by examiner

*Primary Examiner*—Margaret Medley
*Assistant Examiner*—Cephia D. Toomer
(74) *Attorney, Agent, or Firm*—Shirley S. Ma, Esq.

(57) ABSTRACT

An overbased magnesium composition deposit control additive for residual fuel oils and turbine fuels is an overbased magnesium sulfonate, carboxylate or phenate or mixtures thereof containing at least 14% and upwards to about 18% by weight of magnesium and containing a succinic anhydride and lower carboxylic acid co-promoter reaction product. The additive when added to fuel oils, such as residual fuel oils containing high asphaltenes, reduces, if not eliminates, magnesium/asphaltene deposits or sediment and the consequential plugging of filters. The additive also reduces, if not eliminates, vanadium caused corrosion in the turbine. The invention is also the process for preparing the overbased composition or deposit control additive, wherein the overbasing reaction incorporates the combination of a lower carboxylic acid, preferably acetic acid and a succinic anhydride, preferably dodecenyl succinic anhydride (DDSA), as the co-promoter.

32 Claims, No Drawings

OVERBASED MAGNESIUM DEPOSIT CONTROL ADDITIVE FOR RESIDUAL FUEL OILS

FIELD OF THE INVENTION

This invention relates to petroleum fuels and deposit control or sediment reducing additives for such petroleum fuels, as well as to the process for making such additives. The invention more specifically relates to additives to control deposits in residual fuel oils and gas turbine fuels containing high amounts of asphaltenes.

BACKGROUND AND DISCUSSION OF THE PRIOR ART

Petroleum fuels such as residual fuel oils and gas turbine fuels contain vanadium contaminants. These contaminants caused corrosion in the engine or turbine blades. The art recognized that by adding relatively large amounts of magnesium, the magnesium would apparently complex the vanadium and reduce corrosion. It was known to add magnesium, as magnesium sulfate (epsom salt), magnesium acetate, magnesium chloride, magnesium oxide or magnesium carbonate to gas turbine fuels containing vanadium to reduce the corrosion in the turbine blades. One such process is disclosed in U.S. Pat. No. 3,994,699, granted Nov. 30, 1966, to Scott.

Another approach was to add a slurry or paint-like suspension containing substantial amounts of magnesium oxide. The suspension desirably contained 25 to 30% by weight of magnesium, but this paint-like suspension required specialized handling and injection equipment to maintain the magnesium oxide in suspension.

A more recent approach to reducing vanadium corrosion is disclosed in U.S. Pat. No. 5,561,977, granted Oct. 8, 1996, to Harada et al. ("Harada"). Harada disclosed the controlled step-wise addition of metal oxides, e.g., MgO, with initial Mg/V ratios of 2 to 5, in a predetermined cycle of turbine operations.

It was also known in the fuel art to use a magnesium-alkoxide-carbonate complex in combination with an oil soluble sulfonate and a carboxylate and/or phenate dispersing agent as a fuel additive for reducing sediment in vanadium-containing fuels, such as is disclosed in U.S. Pat. No. 4,056,479, granted Nov. 1, 1977, to Redmore et al. ("Redmore"). While the Redmore additives had a magnesium content of about 12.5% to about 14.6%, they generally had undesirable high viscosities.

The fuel art was thus directed to an increased magnesium content additive with practical viscosities.

One attempt to achieve this was to modify the process disclosed in U.S. Pat. No. 4,129,589, granted Dec. 12, 1978, to Eliades et al. ("Eliades"). Eliades disclosed a process for preparing overbased magnesium sulfonate detergents using a promoter system comprised of a lower carboxylic acid, particularly acetic acid, water, and optionally a lower alkanol. The overbased products disclosed in Eliades generally contained only about 9% to 10% by weight of magnesium but were successful detergents for lubrication or engine oils. With controlled or tailored process parameters, the Eliades process produced an overbased product having upwards to no more than about 14% by weight of magnesium with a viscosity below about 200 cSt at 100° C. The Eliades increased magnesium content product had practical viscosities, and achieved acceptance as a fuel oil additive.

Heretofore it was recognized that treating a low (up to about 1% by weight) asphaltene, low aromatic hydrocarbon liquid with an overbased magnesium sulfonate reduced limited asphaltene fouling. This treatment is disclosed in U.S. Pat. No. 4,931,164, granted Jun. 5, 1990 to Dickakian.

More recently it was found that fuel oils, such as residual fuel oils, which contained both high asphaltenes (at least more than 1%, and generally at least 3 to 4% by weight) and highly overbased magnesium sulfonates would, under adverse storage conditions, particularly with water present, produced deposits or sediment containing both magnesium and asphaltenes. This magnesium/asphaltene deposit or sediment plugged the fuel filters. That is, the addition of increased magnesium, while addressing the vanadium corrosion problem, would in combination with high amounts of asphaltenes, cause extensive deposit or sediment.

The fuel art was then faced with the predicament of producing higher magnesium content additives to reduce vanadium contaminant corrosion in the turbine, while where high asphaltenes are present, nonetheless also reduce high magnesium/asphaltene sediment which plugged filters upstream of the turbine.

The fuel art thus desired a high magnesium (i.e., in excess of 14% by weight) additive for a residual fuel oil which reduced, if not eliminated, high magnesium/asphaltene sediment with consequential filter plugging, and yet such high magnesium additive would nonetheless have practical viscosities precluding specialized handling, while also being cost effective.

SUMMARY OF THE INVENTION

This invention is a novel high magnesium content overbased magnesium composition, particularly as a deposit control additive for fuels or fuel oils containing deposit or sediment forming contaminants, particularly asphaltenes. The additive reduces such deposits and the consequential plugging of filters. The invention in another aspect is a fuel oil, such as a residual fuel oil or gas turbine fuel, which contains high amounts of deposit or sediment producing contaminants such as asphaltenes, in combination with the overbased magnesium deposit control additive, which resultant fuel oil has reduced, or is substantially free of, magnesium/asphaltene deposits. The invention in still another aspect is the process for producing such overbased magnesium deposit control additives.

The overbased magnesium additive of the present invention, more specifically, has a magnesium content of at least about 14% by weight, and preferably 14% to 18% or more by weight, and also has a succinic anhydride and lower carboxylic acid overbased co-promoter reaction product. The high magnesium content product is a particularly effective additive for fuel oils, such as residual fuel oils and gas turbine fuels, which contain high amounts of deposit forming contaminants, particularly including asphaltenes and water. This additive when added to fuel oils containing more than 1% or 3 to 4% or more by weight of asphaltenes reduces, if not eliminates, magnesium/asphaltene deposits or sediment. The fuel oil particularly a gas turbine fuel, as previously discussed, contains vanadium corrosion causing contaminants as well. The additive when added in amounts of 2.5:1 to 3:1 of Mg:V, reduces, if not eliminates, both the vanadium caused corrosion and the magnesium/asphaltene caused sediment.

The process for producing the overbased magnesium additive, in broad terms, comprises mixing a sulfonic acid, phenol or carboxylic acid or salt thereof, a magnesium oxide and a co-promoter comprising a lower carboxylic acid and a succinic anhydride, as well as water, a lower alcohol and a solvent, and contacting the mixture with an acidic gas such as carbon dioxide at 50° F. up to the reflux temperature of the mixture to overbase the reaction mixture. The succinic anhydride may be added prior to, during or post carbonation. The volatile components are removed from the overbased mixture to form the highly overbased magnesium additive.

DESCRIPTION OF THE PREFERRED EMBODIMENTS

The terms "succinic anhydride and lower carboxylic acid overbased co-promoter reaction product" as used hereinbefore and hereinafter means that on analysis residues of both the lower carboxylic acid and succinic anhydride are found to be present in the overbased magnesium additive.

The invention in one embodiment is the combination of a fuel oil containing high asphaltenes contaminant with a high magnesium content additive comprising a highly overbased magnesium composition comprising a succinic anhydride and lower carboxylic acid copromoter reaction product. The additive contains at least about 14% and upwards to about 18% or more by weight of magnesium. The fuel oil generally contains vanadium contaminant as well. The additive, when present in amounts of magnesium:vanadium of at least about 2.5:1 to about 3:1 or more, reduces, if not eliminates, the vanadium caused corrosion and asphaltene contaminant caused deposit or sediment.

The overbased magnesium additive desirably has a viscosity of from no more than about 100 cSt upwards to 500 cSt at 100° C., and preferably about 40 cSt to 200 cSt at 100° C., and most preferably no more than about 150 cSt at 100° C. This viscosity is most practical in relation to handling the additive and in fuel oil storage and transport.

The overbased magnesium additive may be in the form of a sulfonate, carboxylate or phenate, or mixtures thereof. The additive is highly overbased and generally has a TBN of at least about 400, and preferably at least 500 to 600 or more. The overbased magnesium sulfonate is the preferred form of the additive.

The overbased magnesium detergent importantly is produced by a novel overbasing co-promoter, namely the combination of a $C_1$ to $C_5$ carboxylic acid, preferably acetic acid, and a succinic anhydride, preferably an alkenyl succinic anhydride and most preferably dodecenyl succinic anhydride (DDSA) and polyisobutenyl succinic anhydride (PIBSA).

The invention in another embodiment is the overbased magnesium composition per se containing the lower carboxylic acid and succinic anhydride co-promoter reaction product.

The invention in still another embodiment is a process for making the high magnesium content overbased magnesium additive comprising (A) mixing a sulfonic acid, a phenol or a carboxylic acid or salt thereof, a magnesium source (e.g., MgO) and a co-promoter comprising a lower carboxylic acid and a succinic anhydride, water, a lower alcohol and a solvent, (B) contacting the mixture with an acidic gas (e.g., $CO_2$) at 50° F. up to the reflux temperature of the mixture to overbase the mixture, and (C) removing volatile components from the overbased product to form the additive. The carbon dioxide is preferably added in a stepwise manner with similar intermittent additions of the succinic anhydride. The succinic anhydride may preferably be added prior to or during carbonation, but may also be added in whole or in part post-carbonation, but the post-carbonation addition is least preferred in providing an effective co-promoter reaction product.

Without wishing to be bound by any theory or mechanism it is believed that the afore-described deposits or sediment is caused by the interaction of magnesium, water and asphaltenes in the fuel oil. While the exact mechanism of this sedimentation is not entirely understood, analyses (by I.C.A.P. Multi-Element Scan, aqua regia digestion) of the metals present in lab (see Table A below) and field (see Table B below) sediments reveal and confirm high magnesium contents:

TABLE A

| Metal | ppm |
| --- | --- |
| Aluminum | 6 |
| Copper | <1 |
| Iron | 18 |
| Tin | 32 |
| Chromium | <1 |
| Lead | <1 |
| Cadmium | <1 |
| Nickel | 2 |
| Zinc | 2 |
| Phosphorous | 5 |
| Calcium | 62 |
| Barium | <1 |
| Magnesium | 5106 |
| Boron | 10 |
| Sodium | <1 |
| Silicon | 181 |
| Potassium | 5 |

TABLE B

| Metal | ppm |
| --- | --- |
| Aluminum | 70 |
| Copper | 31 |
| Iron | 777 |
| Chromium | 13 |
| Lead | 41 |
| Cadmium | 74 |
| Nickel | 25 |
| Zinc | 64 |
| Phosphorous | <1 |
| Calcium | 1027 |
| Barium | 35 |
| Magnesium | 47105 |
| Boron | 41 |
| Sodium | 255 |
| Silicon | 134 |
| Potassium | 11 |

These analyses demonstrate that magnesium is a major component of the filter plugging sediment. This sediment not only plugs filters causing downtime and the need for filter cleaning, but also removes costly magnesium needed to complex with vanadium and reduce the vanadium caused turbine blade corrosion.

The sediment is also believed to be formed by high amounts of asphaltenes in the fuel oil. "High asphaltenes" as used herein is understood to mean at least 1% and usually 3 to 4% by weight, or more, as may be present in residual fuel oils and turbine fuels, and up to 8% by weight, as may be present in boiler fuels, such as No. 6 fuel oil.

This high asphaltenes and high magnesium in the presence of water is believed to be the sediment causation which is effectively reduced or eliminated by the additives of the present invention. The reactants and reaction conditions for producing the deposit control additives are further described as follows:

Lower Carboxylic Acid (Co-Promoter)

The lower carboxylic compound or acid is represented by formula (I):

$$XCOOY \qquad (I)$$

wherein X is —H, —CH$_2$OH, —CH$_2$Cl, —CH$_2$Br, —CH$_2$COCH$_3$ or R.

and Y is H, R or M$_n$ where R is an alkyl radical of from 1 to 4 carbon atoms, the sum of all the carbon atoms in the R radicals not exceeding 5, and M$_n$ is an alkali or alkaline earth metal atom wherein n is an integer of 1 or 2.

Preferred lower carboxylic compounds of this invention are essentially oil-insoluble compounds, such as acetic acid, propionic acid, butanoic acid, glycine, chloroacetic acid, bromoacetic acid, glycolic acid, ethyl acetoacetate, sodium acetate, calcium acetate and magnesium acetate. These formula (I) compounds may be used individually or in combination with one another where the amount of this promoter ranges from 0.5 up to 5 equivalents per equivalent of oil-soluble sulphonic acid, phenol or carboxylic acid. Preferably, the amount ranges from 0.7 to 1.3 equivalents. It has been found in most instances that if over 5 equivalents of the promoter are used, the reaction mixture becomes very viscous and although a product is obtained, the viscosity of the mixture makes the isolation of the product and the introduction of acidic gas into the mixture during the latter part of the process difficult.

Succinic Anhydride (Co-Promoter)

Succinic anhydride promoters are disclosed in U.S. Pat. No. 4,647,387, granted Mar. 3, 1987 to Muir. Useful succinic anhydrides include alkyl and alkenyl succinic anhydrides, as well as succinic anydride derivatives. Preferred embodiments are the alkenyl succinic anhydrides including dodecenyl succinic anhydride (DDSA), tetradecenyl succinic anhydride, n-octenyl succinic anhydride, nonenyl succinic anhydride, polyisobutenyl succinic anhydride (PIBSA), and the like. Suitable succinic anhydride derivatives include the acids, esters, half-esters, double-esters and other hydrolyzable derivatives. While succinic anhydrides having organic radicals of up to about C$_{70}$ may be useful, it is preferred that the organic radical of the succinic anhydride or its derivative be C$_6$–C$_{20}$, and most preferably C$_8$–C$_{18}$. The most preferred alkenyl succinic anhydrides are DDSA and PIBSA.

It has been found that the total amount of succinic anhydride or succinic anhydride derivative required as a promoter or copromoter in the carbonating mixture is 0.5 to 5.0% by weight, and preferably 1.5 to 3.0% by weight.

Water

The total amount of water added to the mixture over the entire reaction time should not exceed 30 equivalents per equivalent of oil-soluble sulphonic acid, phenol or carboxylic acid overbasing reactant. The optimum amount of water to be used is determined by the amount of magnesium oxide used and the metal ratio desired because a larger amount of water results in a product having a higher metal ratio.

Alcohol

The alcohols used in this process include lower aliphatic alkanols, alkoxy alkanols, and mixtures thereof, where the number of carbon atoms does not exceed 5. Examples of the alcohols include methanol, ethanol, isopropanol, n-propanol, butanol and pentanol. The preferred alcohol is methanol because of the low cost and ease of removal from the reaction mixture. Examples of the alkoxy alkanols include methoxy ethanol and ethoxy ethanol.

In order to initiate absorption of the acidic gas in the reaction mixture, it is not necessary to have an alcohol present in the initial mixture. It is believed, however, that the primary function of the alcohol is to promote the stability of the colloidal dispersion of magnesium salts in the oil. To this end there may be none or a small amount of alcohol in the initial reaction mixture and during the contacting with the acidic gas, further amounts of alcohol are added either separately or in combination with the addition of water. It has been found that lower metal ratios result if the total amount of alcohol to be added exceeds 35 equivalents per equivalent of sulphonic acid. The preferred amount to be used ranges from 4 to 20 equivalents per equivalent of sulphonic acid.

Sulphonic Acid (Sulphonate)

The sulphonic acids to be used in this process are those which are widely known by those skilled in the art as oil-soluble sulphonic acids. Such compounds may be derived from natural petroleum fractions or various synthetically prepared sulphonated compounds. Typical oil-soluble sulphonic acids which may be used include: alkane sulphonic acids, aromatic sulphonic acids, alkaryl sulphonic acids, aralkyl sulphonic acids, petroleum sulphonic acids such as mahogany sulphonic acid, petroleum sulphonic acid, paraffin wax sulphonic acid, petroleum naphthene sulphonic acid, polyalkylated sulphhonic acid, and other types of sulphonic acids which may be obtained by fuming sulphuric acid treatment of petroleum fractions. It is understood, of course, that mixtures of the sulphonic acids may be used in preparing an overbased magnesium sulphonate.

In general the reaction of the present invention is carried out by mixing the sulfonic acid, generally a linear alkyl benzene sulfonic acid, with mineral oil and naphtha diluents (25 to 80% by weight of the carbonation mixture).

Carboxylic Acid (Carboxylate)

Carboxylic acid or an acid anhydride, acid chloride or ester thereof, is one wherein said acid has the following formula (II):

(II)

wherein R$^4$ is a C$_{10}$ to C$_{24}$ alkyl or alkenyl group and R$^5$ is hydrogen, a C$_1$ to C$_4$ alkyl group or a —CH$_2$COOH group, or a di- or polycarboxylic acid containing from 36 to 100 carbon atoms or an acid anhydride, acid chloride or ester thereof. Preferably R$^4$ is an unbranched alkyl or alkenyl group. Preferred acids of formula (II) are those wherein R$^5$ is hydrogen and R$^4$ is a C$_{10}$ to C$_{24}$, more preferably a C$_{18}$ to C$_{24}$ unbranched alkyl group. Examples of suitable saturated carboxylic acids of formula (II) include capric, lauric, myristic, palmitic, stearic, isostearic, archidic, behenic and lignoceric acids. Other suitable carboxylic acids include alkyl salicylic acids. Mixtures of acids may also be employed, for example, rape top fatty acids. Particularly suitable mixtures of acids are those commercial grades containing a range of acids, including both saturated and unsaturated acids. Such mixtures may be obtained synthetically or may be derived from natural products, for example, tall, cotton, ground nut, coconut, linseed, palm kernel, olive, corn, palm, castor, soyabean, sunflower, herring and sardine oils and tallow. Sulphurized acids and acid mixtures may also be employed. Instead of, or in addition to, the carboxylic acid there may be used the acid anhydride, the acid chloride or the ester derivatives of the acid, preferably the acid anhydride. It is preferred, however, to use a carboxylic acid or a mixture of carboxylic acids. A preferred carboxylic acid of formula (II) is stearic acid.

Phenol (Phenate)

The phenols and alkyl phenols useful in the present invention are those well known in the art and well disclosed in Wollenberg et al., U.S. Pat. No. 5,330,664, granted Jul. 19, 1994 ("Wollenberg"); Chan, U.S. Pat. No. 4,664,824, granted May 12, 1987; and Campbell, U.S. Pat. No. 5,318,710, granted Jun. 7, 1994. The invention also contemplates sulfonated alkylated phenols such as those disclosed in Wollenberg.

The phenols are incorporated in the reaction mixture in amounts as afore-described and as are well known to those skilled in the art.

Acidic Gas (Carbon Dioxide)

As is appreciated by those skilled in the art, various types of acidic gases may be used in over-basing magnesium sulphonates, carboxylates and phenates. The preferred acidic gases are carbon dioxide, sulphur dioxide, nitrogen dioxide, and hydrogen sulphide. These gases are bubbled through the reaction mixture as it is being mixed so that the selected gas or gases become intimately mixed and in contact with the components of the reaction mixture, and as otherwise described herein.

Magnesium Oxide

The type of magnesium oxide used in a preferred embodiment of the process is the light or active form. Such magnesium oxides have been sold under the trade marks: MAGNESITE, available from Martin Marietta Chemicals, Hunt Valley, Md.; MICHIGAN No. 3, MICHIGAN No. 15, MICHIGAN No. 340, available from Michigan Chemical Corp., Chicago, Ill.; DOW L-2, DOW C-1, available from Dow Chemical Co., Midlane, Mich.; ELASTOMAG 170, and ELASTOMAG 20, available from Morton Chemical Co., Chicago, Ill.; MAGLITE Y, available from Whitacker, Clark and Daniels, South Plainfield, N.Y.; LYCAL 93/711, and LYCAL 96/575, available from Pigment and Chemicals, Toronto, Canada; and MAGOX PREMIUM. The presently preferred magnesium oxides are MAG PLUS Grade 30-325, manufactured by National Magnesia Chemical, a division of National Refractories & Minerals Corporation; MAGOX 98 HR, manufactured by Premier Services Corporation, Middleburg Heights, Ohio (MAGOX is a registered trademark of Premier Services); and MAG CHEM 40, manufactured by Martin Marietta, Hunt Valley, Md. (MAG CHEM is a registered trademark of Martin Marietta).

The amount of magnesium oxide used is dependent upon the metal ratio desired in the final product. The metal ratio is the ratio of the number of equivalents of magnesium in the overbased compound to the equivalents of acid in the overbased compound. Therefore, to obtain a metal ratio of, for example, 30, there must be at least thirty equivalents of magnesium oxide per equivalent of acid in the initial reaction mixture. It is apparent that when the reaction is carried out under less favorable conditions at lower efficiencies, an excess of magnesium oxide beyond that determined by the metal ratio should be used to ensure sufficient incorporation of magnesium with the structure of the overbased magnesium salt of the acid.

Diluent

Several different types of volatile and non-volatile diluents may be used in this process. The non-volatile diluents are generally mineral or synthetic lubricating oils, such as lubricating oils having a viscosity around 100 SUS at 100° F. or higher. The volatile diluents which are iinert to the reaction are preferably hydrocarbons with boiling points ranging from 150° to 300° F. These can be aliphatic, aromatic or a mixture of both types of solvents. For example, naptha is a particularly useful diluent. Other types of suitable diluents include Stoddard solvents, cycloaliphatic and aromatic hydrocarbons, and corresponding halogenated hydrocarbons, such as chlorobenzene, and other conventional organic diluents generally employed in the overbasing procedures in this particular art of manufacture. The amount of diluents used is sufficient to lower the viscosity of the reaction mixture to facilitate mixing thereof during the introduction and contacting of the acidic gases with the mixture.

The initial reaction mixture should have at least traces and preferably up to 2 equivalents of water per equivalent of sulfonic acid. The mixture may have up to 15 equivalents of water where the preferred range in the initial mixture is from 2 to 8 equivalents of water per equivalent of sulfonic acid.

Although the mechanism of the reaction is not fully understood, it is theorized that the presence of water in the reaction mixture initiates absorption of the acidic gas by the reaction mixture. There is, however, a competing reaction for the water in the formation of hydroxides of the magnesium oxide. It is therefore preferred to minimize the reaction of water with the magnesium oxide by carrying out additions of small amounts of water to the reaction mixture during the time that the acidic gas is contacted with the reaction mixture so as to ensure that water is available in the system to promote the absorption of the acidic gas. The amount of water used determines to a certain extent the value of the metal ratio in that higher amounts of water used gives a higher metal ratio; however, with higher amounts of water, there is usually a resultant haziness in the product. On the other hand, a deficiency of water causes higher viscosity in the reaction mixture and a lower metal ratio.

The length of time that the acidic gas is contacted with the reaction mixture depends upon the desired level of magnesium in the overbased magnesium product. The contacting of the gas with the mixture may be continued until no further gas is absorbed to indicate that substantially all of the magnesium oxide originally introduced into the system has been reacted to form an overbased magnesium product. To determine when the absorption of the gas is complete, the flow rate of the acidic gas being introduced is compared to the flow rate of the gas leaving the system. When the flow rate of leaving gas almost equals the flow rate of the introduced gas, then the absorption is substantially complete.

Generally, light magnesium oxide in a stoichiometric excess to react with the sulfonic acid is added to the solution, followed by the addition of water (0.3 mol–10 mol/mol MgO), alkanol (0.1 mol–4 mol/mol MgO), DDSA and lower carboxylic acid (acetic acid) co-promoter (in amounts as afore-discussed). The mixture is stirred vigorously and heated to 100° to 145° F., and up to the reflux temperature of the mixture, whereupon $CO_2$ is bubbled slowly into the reaction mass. Carbonation is generally continued for about 2–4 hours until the consumption of $CO_2$ is essentially complete. During carbonation additional amounts of water and alkanol may be added.

As can be appreciated by those skilled in the art, impurities and other variations in the selected petroleum feed stocks and magnesium oxides, according to this invention, can cause the resultant product to have slightly different metal ratios than that achieved in the following Examples. These Examples are intended to illustrate various aspects of the invention and are not intended to limit the scope of the invention in any way. In all the Examples and as aforesaid the term "TBN" (Total Base Number) is used, and is expressed in mg KOH/g as measured by the method of ASTM D2896. Viscosities were measured by the method of ASTM D445.

The Sediment Test employed in the Examples is as follows:

Sediment Test

Reagents and Materials 1. 1000 ml Erylenmeyer Flask Reservoir with a bottom outlet;
2. 47 mm Inline Filter Holder;
3. 200 Mesh (75 micron) Stainless Steel Filter Screen cut to fit the Inline Filter Holder;
4. Magnetic Mixer and Heater with Thermocouple Controller;
5. Peristaltic Pump;
6. Assorted Tubing;
7. Analytical Balance (0.1 mg);
8. Top Loading Balance (0.1 g);
9. Microscope (20–80 Zoom Magnification);
10. Heptane.

Procedure

1. Weigh 850 grams of test Fuel Oil into the reservoir. Use the Top Loading Balance.
2. Install a clean weighed 200 Mesh Filter Screen in the Inline Filter Holder. Weigh the filter screen to 0.1 mg on the Analytical Balance.
3. Weigh enough additive into the reservoir to provide 60 ppm Magnesium. Weigh on the Top Loading Balance.
4. Connect tubing between the Inline Filter Holder and Peristaltic Pump for recirculation.
5. Heat the reservoir Fuel to 75° C. and mix at 1000 RPM.
6. Start the Peristaltic Pump recirculating at approximately 160 ml/min.
7. Recirculate 100 liters of fuel from the reservoir. This will take approximately 10.5 hours.
8. Turn off the recirculation and drain Fuel Oil from the lines and filter by draining back to the reservoir.
9. Open the filter. Remove the screen and wash with heptane.
10. Examine the filter screen for weight and type of sediment. Use a microscope and determine if sediment is debris or gel.
11. Reinstall the filter screen.
12. Add 60 ppm Magnesium and 1 gram of Water.
13. Repeat step 4 to step 11. Recirculate 75 liters of Fuel from the reservoir (approx 7.5 hours).
14. Add 60 ppm Magnesium to 1 gram of Water.
15. Repeat step 4 to step 11. Recirculate 75 liters of Fuel from the reservoir (approx 7.5 hours.)
16. Stop the test.
17. Report the amount and type of sediment after each of the 3 recirculation stages (100 liter/75 liter/75 liter). Weigh the filter screen to 0.1 mg on the Analytical Balance.

Calculation $1^{st}$ Recirculation: Report weight of sediment+type of sediment $2^{ND}$ Recirculation: Report weight of sediment+type of sediment $3^{RD}$ Recirculation: Report weight of sediment+type of sediment Total sediment weight=$3^{rd}$ recirculation sediment weight Specification Pass=up to 25 mg sediment Fail=Greater than 25 mg sediment and any gel Note: If pressure builds up, stop the test and examine the filter screen. The test is deemed an automatic failure.

EXAMPLE 1

The following overbasing mixture was prepared:

| Component | Parts by weight |
| --- | --- |
| Sour oil (sulfonic acid) | 89.8 |
| Diluent (fuel oil) | 41.5 |
| DDSA | 3.5 (2%) |
| Solvent (Iosol) | 195 |
| MgO | 48 |
| Methanol | 6.1 |
| Water | 9.5 |
| Acetic acid | 18.2. |

The overbasing mixture was initially at 45 to 55° C. The mixture was carbonated with $CO_2$ in step wise additions of 300 ml/min, 150 ml/min and 90 ml/min over 4 hours, and refluxed. The overbased mixture was filtered and stuffed. Diluent fuel oil in the amount of 16.8 grams was added. The overbased magnesium sulfonate product had a TBN of 630, and a viscosity of 143 Cst at 100° C., with the viscosity measured with the sulfonate at a TBN of 560.

A control sample was prepared as aforesaid but without any DDSA.

A comparison of the use of the overbased products with 2% DDSA and without any DDSA in a fuel oil, demonstrated that whereas the overbased product without DDSA produced encrustations and black sludge or sediment build up the overbased product with 2% DDSA co-promoter showed only a small amount of encrustation with no black sludge or sediment build up.

EXAMPLE 2

The following overbasing mixture was prepared:

| Component | Parts by weight |
| --- | --- |
| Sour oil (sulfonic acid) | 89.8 |
| Diluent (fuel oil) | 41.5 |
| PIBSA | 3.5 (2%) |
| Solvent (Iosol) | 195 |
| MgO | 48 |
| Methanol | 6.1 |
| Water | 9.5 |
| Acetic acid | 18.2. |

The overbasing mixture was initially at 45 to 55° C. The mixture was carbonated with $CO_2$ in step wise additions of 300 ml/min, 150 ml/min and 90 ml/min over 4 hours, and refluxed. The overbased mixture was filtered and stuffed. Diluent fuel oil in the amount of 16.8 grams was added. The overbased magnesium sulfonate product had a TBN of 630, and a viscosity of 142 Cst at 100° C., with the product measured at a TBN of 560.

A control sample was prepared as aforesaid but without any PIBSA.

A comparison of the use of the overbased products with 2% PIBSA and without any PIBSA in a fuel oil, demonstrated that whereas the overbased product without PIBSA produced encrustations and black sludge or sediment build up.

EXAMPLE 3

The following overbasing mixture was prepared:

| Component | Parts by weight |
|---|---|
| Naphtha | 80.0 |
| Fuel Oil No. 2 | 27.0 |
| Water | 5.4 |
| Methanol | 3.5 |
| Mag Chem 40 (MgO) | 26.8 |
| Sulfonic Acid | 51.5 |
| (@ 25.5% AI; 24.4% Oil; 51.1% Vol.) | |

The foregoing components were mixed and the temperature adjusted to 30° C. The acetic acid co-promoter was then added as follows.

| | |
|---|---|
| Acetic acid, 92% | 8.7. |

Carbonation was started immediately after the acetic acid addition.

Carbonation was continued as follows:

at 172 ml/min for 30 minutes.

at 86 ml/min for 90 minutes.

at 43 m/min for 120 minutes.

The carbonation temperature was maintained at 42 to 54° C.

During carbonation the following succinic anhydride co-promoter was added as follows:

| (a) after 40 minutes: | |
|---|---|
| Water | 6.3 |
| DDSA | 2.0; |

| (b) after 80 minutes: | |
|---|---|
| Water | 6.3. |

After carbonation, the overbased product was cooled to below 35° C. The product was then filtered and stripped. A control was produced according to the foregoing but without the addition of any DDSA or other succinic anhydride. The samples with and without DDSA were subject to the foregoing Sediment Test and the results reported in Table 3.

TABLE 3

| Results | | |
|---|---|---|
| | Example 3 | Control |
| Magnesium, wt % | 14.2 | 14.2 |
| DDSA, wt. % | 2 | zero |
| Sp. Gr. @ 15° C. | 1.246 | 1.24 |
| Magnesium Sulfonate, wt % | 13.7 | 13.0 |
| TBN, mg KOH/gm | 570 | 550 |
| TAV | 641 | 640 |
| Viscosity, cSt @ 100° C. | 41.6 | 90 |
| Sediment, Vol. % | 0.03 | 0.04 |
| Water, Vol.% | 1.0 | 1.0 |
| Flash Point, PMCC ° C. | 66 | 66 |

TABLE 3-continued

| Results | | |
|---|---|---|
| | Example 3 | Control |
| Sediment Test | No sediment Pass at 0.5% water | Sediment Fails at 0.2% water |

The results of Table 3 demonstrate that the additive with the acetic acid—succinic anhydride co-promoter reaction product eliminated sediment, whereas a comparable sample with only the acetic acid promoter failed the Sediment Test even with a lesser amount of water.

While the Examples are described for an overbased magnesium sulfonate additive, it is within the contemplation of this invention to provide overbased magnesium phenate and carboxylate, particularly including salicylate, deposit control additives, as well as mixtures thereof.

What is claimed is:

1. A deposit controlled fuel oil comprising;
   (a) a fuel oil comprising a deposit producing contaminant comprising more than 1% by weight of asphaltenes; and
   (b) an asphaltene deposit control additive comprising; a Mg overbased sulfonate, phenate or carboxylate including a succinic anhydride and lower carboxylic acid co-promoter reaction product;
   wherein the fuel oil with the additive substantially reduces said deposits.

2. The fuel oil of claim 1, wherein the fuel oil further comprises vanadium, and said additive being present in an Mg:V molar ratio of at least about 2.5:1.

3. The fuel oil of claim 1, said additive having a viscosity of about 40 to 200 cSt at 100° C.

4. The fuel oil of claim 1, said lower carboxylic acid comprising a $C_1$ to $C_5$ carboxylic acid.

5. The fuel oil of claim 4, said carboxylic acid comprises acetic acid.

6. The fuel oil of claim 1, wherein said succinic anhydride comprises an alkenyl succinic anhydride.

7. The fuel oil of claim 6, said alkenyl succinic anhydride comprises dodecenyl succinic anhydride.

8. The fuel oil of claim 1, said composition comprising 14% to 18% by weight magnesium.

9. The fuel oil of claim 1, wherein fuel oil comprises 3 to 4% by weight of asphaltenes, and the fuel oil with the additive is substantially free of magnesium/asphaltene deposits.

10. The fuel oil of claim 1, said additive having a TBN of at least about 500 to 600.

11. The fuel oil of claim 10, said additive comprising a magnesium content of at least about 14% by weight.

12. The fuel oil of claim 10, said lower carboxylic acid comprising a $C_1$ to $C_5$ carboxylic acid.

13. The fuel oil of claim 10, said carboxylic acid comprising acetic acid.

14. The fuel oil of claim 10, said succinic anhydride comprising an alkenyl succinic anhydride.

15. The fuel oil of claim 14, said alkenyl succinic anhydride comprising dodecenyl succinic anhydride.

16. The fuel oil of claim 14, said alkenyl succinic anhydride comprising polyisobutenyl succinic anhydride.

17. An asphaltene deposit control additive comprising a Mg overbased sulfonate, phenate or carboxylate including a succinic anhydride and lower carboxylic acid co-promoter reaction product.

18. The additive of claim 17, said additive having a magnesium content of at least 14% by weight and a viscosity of about 40 to 200 cSt at 100° C.

19. A process for making an asphaltene deposit control additive comprising:
   (A) admixing;
      (a) at least one selected from a sulfonic acid, a phenol and a carboxylic acid, or salt thereof,
      (b) magnesium oxide, and
      (c) a promoter system comprising;
         (i) a $C_1$ to $C_5$ carboxylic acid in a co-promoter amount,
         (ii) a succinic anhydride in a co-promoter amount,
         (iii) water,
         (iv) a $C_1$ to $C_5$ alcohol, and
         (v) a solvent;
   (B) contacting the mixture of step (A) with carbon dioxide, said contacting being at a temperature up to the reflux temperature of the mixture to overbase the mixture; and
   (C) removing volatile components from the overbased mixture of step (B) to form the additive.

20. The process of claim 19, said additive comprising an overbased magnesium sulfonate.

21. The process of claim 19, said additive comprising about 14% to 18% by weight of magnesium.

22. The process of claim 19, said additive having a viscosity of 40 to 200 cst at 100° C.

23. The process of claim 19, said $C_1$ to $C_5$ carboxylic acid comprising acetic acid.

24. A process for making a fuel oil asphaltene deposit control additive comprising:
   admixing;
      (a) a least one selected from a sulfonic acid, a phenol and a carboxylic acid or salt thereof;
      (b) magnesium oxide;
      (c) a first co-promoter comprising:
         (i) a $C_1$ to $C_5$ carboxylic acid in a co-promoter amount;
         (ii) water;
         (iii) a $C_1$ to $C_5$ alcohol; and a solvent; and
      (d) a second co-promoter comprising:
         (i) a succinic anhydride in a co-promoter amount; contacting a mixture of (a), (b), (c) and (d) with an acidic gas at a temperature up to the reflux temperature to overbase the mixture; and removing volatile components from the overbased mixture to form the asphaltene deposit control additive.

25. The process of claim 24, wherein the succinic anhydride comprises an alkenyl succinic anhydride.

26. The process of claim 25, wherein the alkenyl succinic anhydride comprises dodecenyl succinic anhydride.

27. The process of claim 24, wherein said $C_1$ to $C_5$ carboxylic acid comprises acetic acid.

28. The process of claim 24, wherein said acidic gas comprises carbon dioxide, and carbonating the mixture.

29. The process of claim 28, further comprising adding the succinic anhydride during said carbonating.

30. The process of claim 28, further comprising adding the succinic anhydride at least in part after carbonating the selected mixture.

31. The process of claim 24, wherein the additive has a viscosity of 40 to 200 cSt at 100° C.

32. The process of claim 24, wherein the temperature is 45° to 55° C. up to the reflux temperature of the mixture, and wherein the produced additive has a TBN of at least about 500 to 600 and a viscosity of 40 to 200 cSt at 100° C.

* * * * *